United States Patent [19]

Trisciani et al.

[11] Patent Number: 4,835,109

[45] Date of Patent: May 30, 1989

[54] PROCESS AND APPARATUS FOR CHEMICAL ANALYSES BY LIQUID CHROMATOGRAPHY

[75] Inventors: Adriano Trisciani, Monza; Rosolino Carera, Soresina, both of Italy

[73] Assignee: Carlo Erba Strumentazione S.p.A., Italy

[21] Appl. No.: 761,908

[22] Filed: Aug. 2, 1985

[30] Foreign Application Priority Data

Nov. 14, 1984 [IT] Italy ................................ 23563 A/84

[51] Int. Cl.$^4$ ........................ G01N 1/14; B01D 15/08
[52] U.S. Cl. .................................... 436/178; 436/161; 422/70; 422/81; 422/82; 422/103; 73/61.1 C; 73/863.83; 73/863.86; 73/864.35; 73/864.21; 73/864.83
[58] Field of Search ............... 422/70, 81, 82, 103; 436/161, 178; 73/61.1 C, 863.83, 863.84, 863.86, 864.35, 864, 864.83

[56] References Cited

U.S. PATENT DOCUMENTS

| | | | |
|---|---|---|---|
| 3,266,321 | 8/1966 | Fenske et al. | 73/863.83 |
| 3,901,653 | 8/1975 | Jones et al. | 73/863.83 X |
| 4,486,097 | 12/1984 | Riley | 422/82 X |

Primary Examiner—Barry S. Richman
Assistant Examiner—Lynn M. Kummert
Attorney, Agent, or Firm—Lerner, David, Littenberg, Krumholz & Mentlik

[57] ABSTRACT

A process and an apparatus for performing analyses in liquid chromatography, by ways of a pump capable of drawing a fluid and injecting it at high pressure, through at least a control valve, into a separation column.

To obtain maximum precision as required by the analysis, before each analysis or each group of analyses, or with respect to each fluid used, a pump stroke is performed with the pump delivery side shut off in order to record and store the characteristics of compressibility of the fluid. These characteristics are kept into consideration in the subsequent operative stages to obtain an exactly constant delivery of the feed pump to the separation column.

8 Claims, 2 Drawing Sheets

PROCESS AND APPARATUS FOR CHEMICAL ANALYSES BY LIQUID CHROMATOGRAPHY

BACKGROUND OF THE INVENTION

1. Field of the Invention

The present invention relates to a process and an apparatus for performing analyses by liquid chromatography, wherein a syringe pump is used for injecting a fluid at high pressure into a separation column. More exactly, the invention relates to a process and apparatus to rectify the plunger stroke of said syringe pump in order to adjust the compressibility of the fluid it contains, whichever the operating pressure value is during an analysis in liquid chromatography.

The apparatus comprises a syringe pump actuated by a motor means and capable of drawing a preset quantity of solvent fluid from a container of same, then sending it, through a control valve, to a sample drawing zone and then to a column of chromatographic separation and finally to a detector.

2. Description of the Prior Art

As it is well known to those skilled in the art, the precision and reliability of liquid chromatography analysis are connected to several factors, the most important of which is the need of exactly controlling the quantity of solvent introduced into the column and consequently the constancy of the fluid flow to the column.

Up to now said delivery constancy was ensured by a motor means continuously acting on the piston pump, for example in the form of a step-by-step motor capable of ensuring a constant piston foward stroke and therefore, theoretically, a constant delivery feeding. However, it must be noticed that pressures involved during these analyses are very high, for example up to values of 500 kg/cm$^2$, i.e. values at which the solvent compressibility, in particular that of certain fluids which are under supercritical temperature and pressure conditions as well as of certain solvents, cannot be disregarded. Amongst those fluids creating heavy problems of compressibility at said high values of pressure, the following can be considered: carbon dioxide, pentane, ammonia, when used under supercritical temperature and pressure conditions, and moreover alcohols, chlorinated, aromatic and aliphatic solvents. In these cases precision of the amount pumped can be lost, in that a constancy in the foward movement of the piston does not correspond to a constancy of delivered flow, because at high pressures said flow rate is reduced due to the solvent compressibility.

OBJECTS OF THE INVENTION

An object of the present invention is to provide a solution to this problem therefore providing a process and an apparatus to obtain more precise and accurate as well as more reliable analyses in liquid chromatography in comparison with those performed up to now.

SUMMARY OF THE INVENTION

According to the invention, said problem is solved by means of a process for performing analyses by means of a liquid chromatography apparatus and comprising, besides the usual process steps, a further step of fluid compression, carried out by a pump stroke, with compression of the fluid contained in the syringe upstream the control valve or valves, which are kept closed, up to a pressure exceeding the one forseeable during the analysis; during said fluid compresssion step, the fluid compressibility values are stored, said stored values being then used during the analytical stage, for the control of the means actuating said pump.

In practice, during said fluid compression stroke a pressure-piston movements curve typical of the fluid treated is stored in a microprocessor. During the subsequent analysis, the microprocessor is set on the delivery value involved and is then capable of controlling the speed of the pump piston keeping into consideration the compressibility of the fluid at the operating pressure each time present during the compression stroke, as well as the fluid volume present at each moment in the pump chamber and other possible factors.

The apparatus according to the invention, for performing chemical analyses by liquid chromatography using said process, comprises, upstream a separation column, at least a switch valve capable of fluidically connecting a suction and force pump, provided with a control means, alternatively to a solvent vessel, to the column or to an exhaust, said apparatus further comprising means for pneumatically sealing the pump delivery side; a pressure transducer for detecting pressure on the pump delivery side; a microprocessor for storing, during a pump compressibility stroke, with a closed pump delivery side, the movements of the movable element of the pump in relation to the pressures recorded by said transducer; and means connecting said microprocessor with said pump control means for controlling the constancy of the pump delivery during the pump operative strokes to send the fluid into the column as a function of the recorded compressibility features for the solvent used, during said compressibility pump stroke. In order to sealingly close the pump delivery side, the same switch valve is advantageously used, said valve having a position in which the duct connecting the same to the pump is closed. As above stated, the pump is preferably a piston pump actuated by a step-by-step motor which is connected to the pump piston by a gear reduction unit and a screw-screw nut connection, a ball circulation connection, or the like. acting on the piston rod.

Said valve typically comprises a head having a series of ducts leading to different points of an internal plane surface, as well as a counter-surface provided with at least a groove to connect the duct coming from the pump with the other ducts or with a closed space, said counter-surface being rotatable on an axis perpendicular to the same, for the orientation of the connecting groove towards the operative positions, and being moreover elastically pressed against the first surface.

BRIEF DESCRIPTION OF THE DRAWINGS

The invention will be now described more in detail with reference to a preferred embodiment of same, illustrated as an example in the accompanying drawings, wherein.

DESCRIPTION OF THE PREFERRED EMBODIMENT

Figure 1:
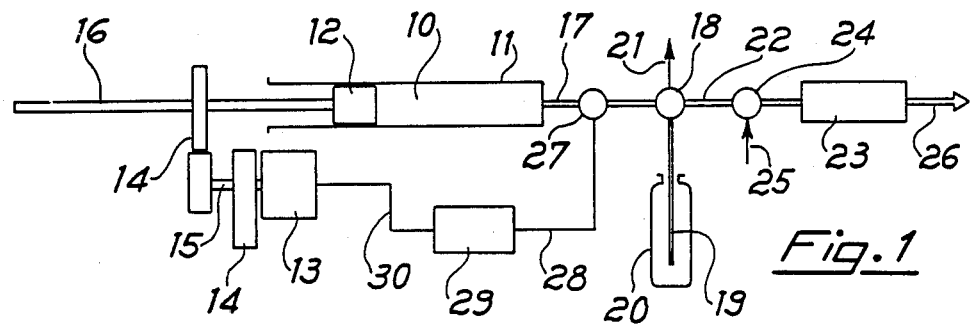
FIG. 1 is a diagrammatic view of an apparatus according to the invention for samplings in liquid chromatography.

With reference first of all to FIG. 1, an apparatus for performing analyses in liquid chromatography is diagrammatically shown.

The apparatus comprises, in a way known in itself, a pump 10 for example consisting of a cylinder 11 and a piston 12, actuated by an actuating means which in the shown example is constituted by a step-by-step motor 13 and by a gear unit 14 reducing the rotation speed of the motor shaft 15 and transforming the rotatory movement into a translation of rod 16 of piston 12. The pump 10 is connected downstream, through a duct 17, with a switch valve 18 capable of connecting said duct 17 alternatively to a duct 19 for drawing the solvent from a container 20, to an exhaust duct 21 and to a duct 22 connecting the separation column 23, through a device 24, known in itself, capable of introducing the sample 25. Downstream of the column 23, the arrow 26 shows the connection to a detector.

As it is known, in liquid chromatography the analyses are performed at pressures of the solvent or fluid introduced through the separation column 23 which reach very high values, for example up to 500 kg/cm$^2$.

Figure 2:
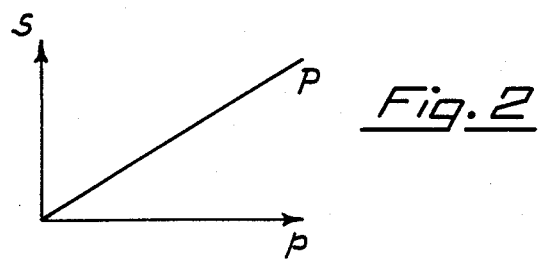
FIG. 2 is an example of a curve: piston movements-pressure, as recorded by a pressure transducer in the apparatus of FIG. 1 and stored in a microprocessor of the same apparatus, for an idle stroke of the pump.

In order to keep into consideration the compressibility of the solvents used, the apparatus comprises, on the duct 17 connecting the pump 10 to the valve 18, a pressure transducer 27 which is able to detect at any moment the pressure values present in the duct 17 and to communicate them, through the line 28, to a microprocessor 29, which also receives the data concerning the movements of piston 12, through the line 30 connecting the motor 13. By performing a plurality of detections it is possible to store in the microprocessor 29 a curve s-p such as the one shown in FIG. 2, in which pressure values are correlated with the movements of piston 12 as obtained with a given fluid solvent, the curve being recorded when the fluid is submitted to a compression stage within the pump 10 and the duct 17, up to pressure values at least corresponding to the ones involved in the sample analyses, by a pump stroke as performed after closure of the duct 17 by means of the valve 18.

In practice, before each analysis or before each group of analyses performed with the same solvent, a step is foreseen during which the desired solvent is drawn from the container 20, the valve 18 is closed and the piston 12 of the pump is moved forward, then the values of pressure and displacement of the same piston 12 at any moment are recorded and stored. After this stage, the analysis goes on normally and the movement of piston 12 is controlled by a direct control of the microprocessor 29 on the step-by-step motor 13 in a way as to maintain a constant and preset value of delivery through the column 23, keeping into consideration the operating pressure, the volume of liquid present at any instant in the pump chamber and finally the compressibility of the solvent which has been stored in the microprocessor 29.

It is possible to foresee a thermoregulation of the syringe in which the mobile phase or solvent is contained to obtain programmed deliveries with the maximum accuracy even if the environmental temperature vaires. The connection of duct 17, coming from the pump, respectively with duct 19 for the solvent drawing, with exhaust duct 21 and with duct 22 leading to the separation column, are controlled by a motorized valve 18, as shown more in detail in FIGS. 3 and 4.

Said valve comprises a body 31 which carries a head 33 fixed by means of bolts 32, and wherein four fittings are inserted, 34, 35, 36 and 37 respectively (FIG. 4), which are connected to the ducts 17, 19, 21 and 22. The fittings 34–37 all lead to a plane surface 38, as diagrammatically indicated by references 39–42 in FIG. 4, the outlet 39 of fitting 34, connected to the pump 10, being positioned centrally with respect to said surface. For the alternative connection of duct 34 with one of the other ducts 35, 36, 37, a counter-surface 43 bearing an elongated groove 44 is resting on the surface 38 (FIG. 4), said counter-surface being capable of fluidically connecting the passage 39 with one of passages 40, 41 and 42 or, if rotated to a position opposite to the one illustrated in FIG. 4, of closing said duct 34 from the external environment.

Figure 3:
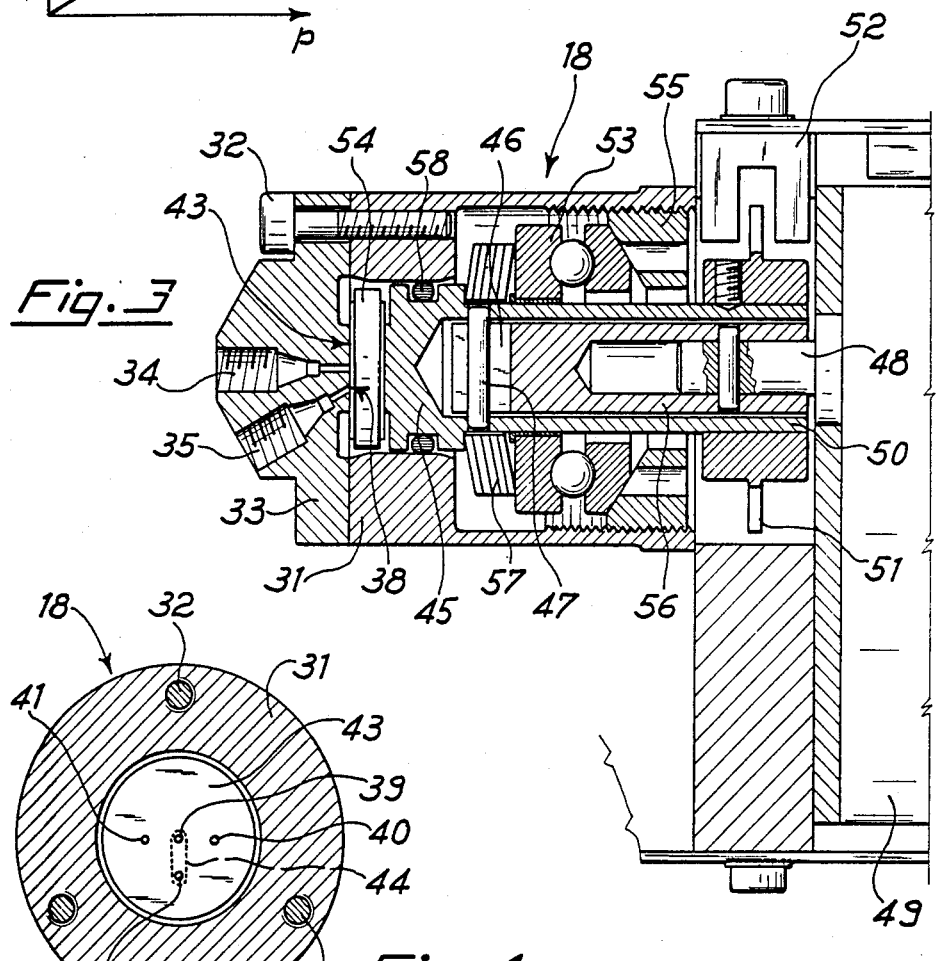
FIG. 3 is a partially cutaway side view of the switch valve of FIG. 1.
Figure 4:
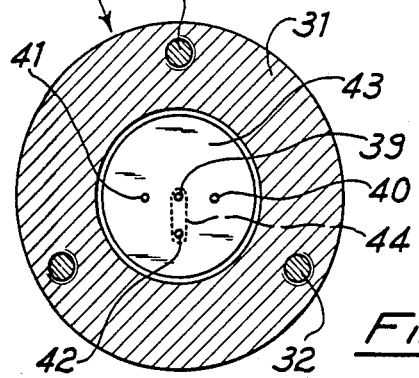
FIG. 4 is a cross section according to line IV—IV of FIG. 3.

As shown in FIG. 3, said counter-surface 43 is carried by a circular plate 54 mounted on a support 45 which on its turn is connected, by means of a slit 46 and a pin 47, to an extension 56 of the shaft 48 of a motor means 49, capable of being rotated for a preset angle. The rotations of counter-surface 43 are controlled by a tubular appendix 50 as shown by the support 45 and provided with fins 51 which pass through a known position detecting device 52 to ensure the utmost precision in the positioning of support 45 and therefore of groove 44. The plate 54 and support 45 are mounted in a rotatory way with respect to the valve body 31 by means of a self-centering thrust bearing 53 which rests on one side on an adjusting nut 55 and is stressed on the other side by a compression spring 57 which bears, on the opposite side, against the support 45, to press the surface 43 against the surface 38 with the desired necessary strength, in order to ensure that no leakage occurs even at very high pressures.

Sealing between the two surfaces is ensured, even in long time periods, by a self-adaptation as determined by a "floating" assembling of support 45 on the shaft 48 of the motor 49. The side sealing to the counter-surface 43 is in any case ensured by gaskets 58. By rotating the shaft 48, the support 45 and the plate 54, it is possible to selectively place the groove 44 in a way as to connect the outlet 39 with outlets 40, 41 and 42 respectively, or in a position in which pump connecting duct 17 is completely closed.

Figure 5:
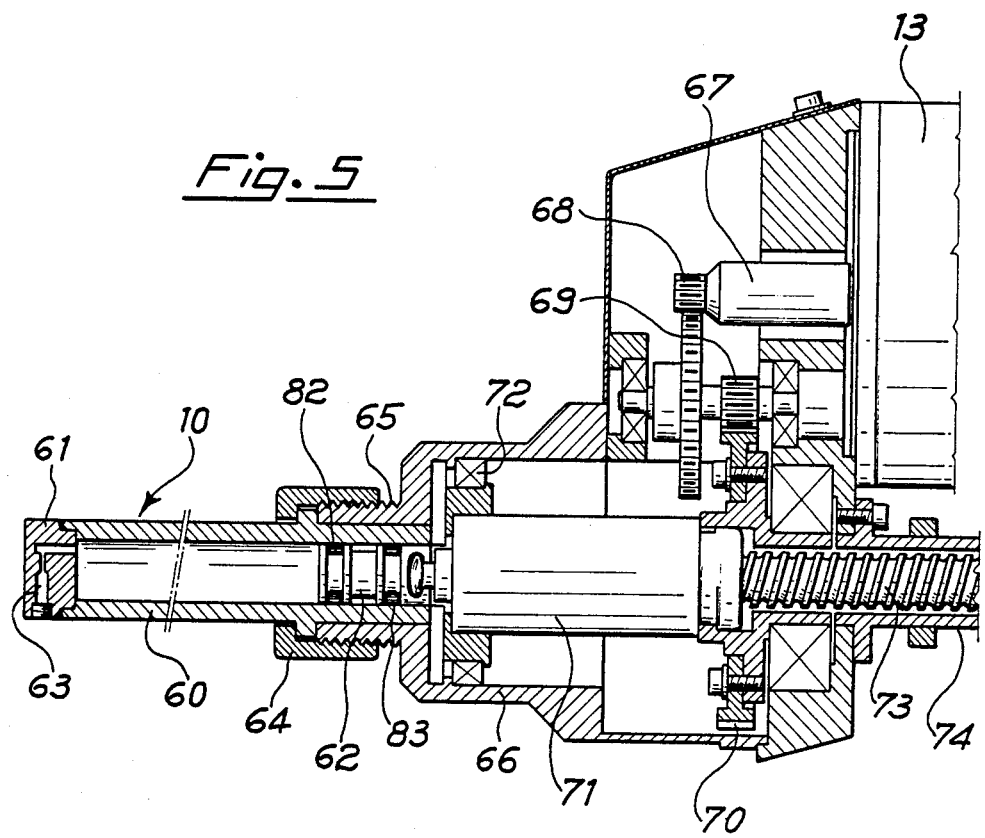
FIG. 5 is a partially cutaway side view of the piston pump and relevant control means.
Figure 6:
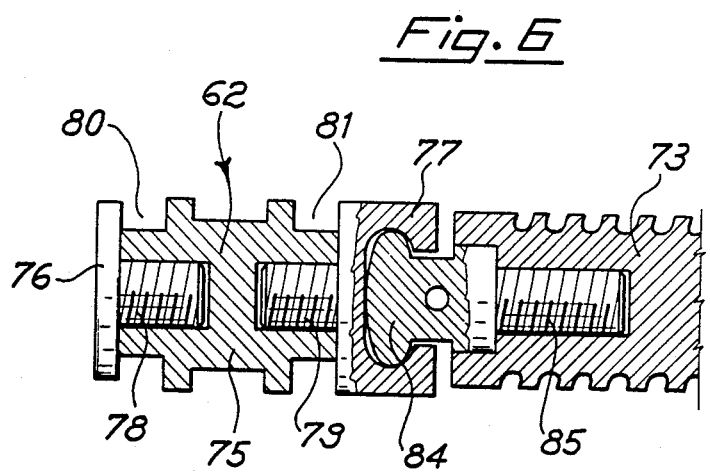
FIG. 6 is an enlarged cross view illustrating the connection between the rod and piston in the pump of FIG. 5.

FIGS. 5 and 6 illustrate some details of pump 10 and of the relevant control motor. The pump 10 essentially consists of a cylinder 60 and piston 62 pump, whose cylinder 60 is closed at one end by a head 61 with a passage 63 to connect the duct 17. On the opposite side, the cylinder 60 is fixedly connected, by a nut 64 screwed on a thread 65, to a bell body 66 which ensures a connection with the step-by-step motor and with a movement reducing and transforming unit. More exactly, the motor 13 has a shaft 67 bearing a pinion 68 which actuates two reducing gears 69 and a ring gear 70 which controls a rectilinear feeding device 71 of the screw-screw nut type, preferably of the ball circulation type, mounted on support 66 by means of a bearing 72. The piston rod 73 has the configuration of a but screw and moves inside the housing 74, said rod 73 being connected to the piston 62 in the way more specifically illustrated in FIG. 6. With reference to said FIG. 6, the piston is formed by a block 75 having two heads 76 and 77 connected for instance by means of screws 78 and 79 in such a way as to form seats 80 and 81 for gaskets 82 and 83 (FIG. 5). The head 77 has a head having an oval shape in section, which houses a shaped head 84 fixed to the rod 73 at 85, the connection between the two heads 77 and 84 being in this case too of the "floating" type and such as to ensure a self-adaptation of the piston 62 in its seat inside the cylinder 60, in order to reduce wear of the gaskets 82 and 83.

We claim:

1. Apparatus for sample analysis by high pressure liquid chromatography in a separation column comprising:
    pump means including a reciprocating piston being selectively connected to a separation column during a delivery phase and disconnected from said separation column during an idling phase, thereby creating pressure in a fluid contained within said pump means during said idling phase and delivering the fluid to said separation column during said delivery phase;
    pump control means for controlling reciprocation of said reciprocating piston;
    valve means for selectively connecting and disconnecting said pump means to and from said separation column;
    pressure transducer means for detecting pressure created in the fluid by said pump means during said idling phase;
    microprocessor means for maintaining a constant delivery of the fluid to said separation column by determining compressibility of the fluid during said idling phase based upon the pressure detected by said pressure transducer means and regulating said pump control means during said delivery phase to control the reciprocation of said reciprocating piston of said pump means based upon the fluid compressibility determination to compensate for the fluid compressibility; and
    connecting means for connecting said microprocessor means to said pressure transducer means during said idling phase and to said pump control means during said delivery phase for control thereof.

2. The apparatus of claim 1 including solvent container means and exhaust means, and wherein said valve means includes connection means for selectively connecting said pump means to said solvent container means and to said exhaust means.

3. The apparatus of claim 1 wherein said pump control means comprises a stepping motor.

4. The apparatus of claim 3 wherein said reciprocating piston includes screw means, and wherein said pump control means includes gear means interconnecting said stepping motor with said screw means.

5. The apparatus of claim 1 wherein said valve means comprises a head including a plurality of duct means including a first duct connected to said pump means and a second duct connected to said separation column, said head further including an internal surface, and rotating plate means including a counter-surface adjacent to said internal surface, said rotating plate means including groove means on said counter-surface, said rotating plate means being rotatably mounted on said valve means whereby said first duct can be selectively connected and disconnected from said second duct by rotating said rotating plate means to selectively align said groove means with said first and second ducts.

6. The apparatus of claim 5 including motor means, said motor means including a rotatable motor shaft, and rotatable motor shaft connection means for connecting said rotatable motor shaft to said rotating plate means for rotation thereof.

7. The apparatus of claim 6 wherein said rotatable motor shaft connection means comprises floating connection means for permitting self-adjustment of said rotating plate means to prevent leakage between said rotating plate means and said head.

8. The apparatus of claim 7 including compression means for mounting a compression force between said rotating plate means and said head.

* * * * *